US006916647B1

(12) United States Patent
Elsser

(10) Patent No.: US 6,916,647 B1
(45) Date of Patent: Jul. 12, 2005

(54) PROTECTIVE CULTURES AND USE THEREOF FOR PRESERVING FOODSTUFFS

(75) Inventor: Dieter Elsser, Bargum (DE)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/958,051

(22) PCT Filed: Apr. 5, 2000

(86) PCT No.: PCT/EP00/03025

§ 371 (c)(1), (2), (4) Date: Jan. 28, 2002

(87) PCT Pub. No.: WO00/60947

PCT Pub. Date: Oct. 19, 2000

(30) Foreign Application Priority Data

Apr. 9, 1999 (DE) ........................................ 199 17 715

(51) Int. Cl.$^7$ ................................................ C12N 1/20

(52) U.S. Cl. .................................. 435/252.1; 435/259.9

(58) Field of Search ................. 426/61, 332; 435/252.9

(56) References Cited

U.S. PATENT DOCUMENTS

| | | | | |
|---|---|---|---|---|
| 3,899,594 A | | 8/1975 | Nickerson et al. | |
| 5,520,933 A | * | 5/1996 | Yoshida et al. | 426/7 |
| 5,750,165 A | | 5/1998 | Erway | |
| 6,063,410 A | * | 5/2000 | Vedamuthu et al. | 426/56 |

FOREIGN PATENT DOCUMENTS

| | | |
|---|---|---|
| EP | 0484991 A2 | 5/1992 |
| JP | 08187071 A | 7/1996 |
| JP | 08187072 A | 7/1996 |

OTHER PUBLICATIONS

"Food and Feed Chemistry," *Chem. Abstr.*, 116:37846V (1992).

"Food and Feed Chemistry," *Chem. Abstr.*, 125(15): 190043M (1996).

"Food and Feed Chemistry," *Chem. Abstr.*, 129(13): 160715X (1998).

* cited by examiner

*Primary Examiner*—Keith Hendricks

(74) *Attorney, Agent, or Firm*—McDermott Will & Emery LLP

(57) ABSTRACT

The invention relates to novel protective cultures, containing lactic acid-producing bacteria for preserving foodstuffs or animal feed, which can only be conserved for a limited period of time, even under refrigeration. The protective cultures can inhibit the growth of bacteria which are dangerous to the consumer, if the cold chain is interrupted, or if the prescribed cooling temperature is exceeded. The invention further relates to foodstuffs or animal feed which contain the inventive protective cultures. The strain *Lactococcus lactis* subsp. *lactis* 1526 is specifically provided.

1 Claim, 6 Drawing Sheets

Figure 1: Behaviour of *Lactococcus lactis ssp. Lactis 1526* during gold storage (6°C/21 days) and subsequent increase in temperature (22°C/2 days)
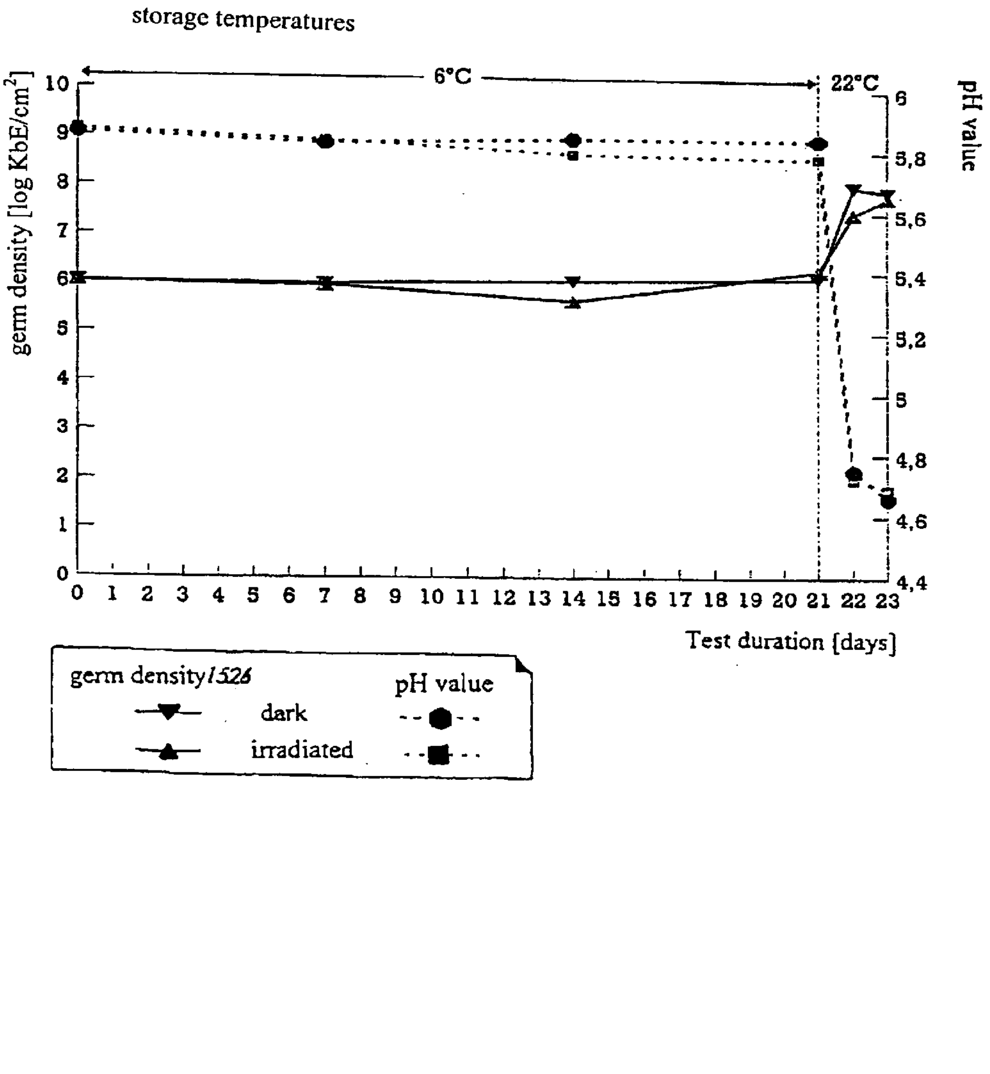

Figure 2: Inhibition of a salmonella pool by *Lactococcus lactis ssp. Lactis 1526* during cold storage (6°C/14 days) and subsequent increase in temperature (22°C/2 days)
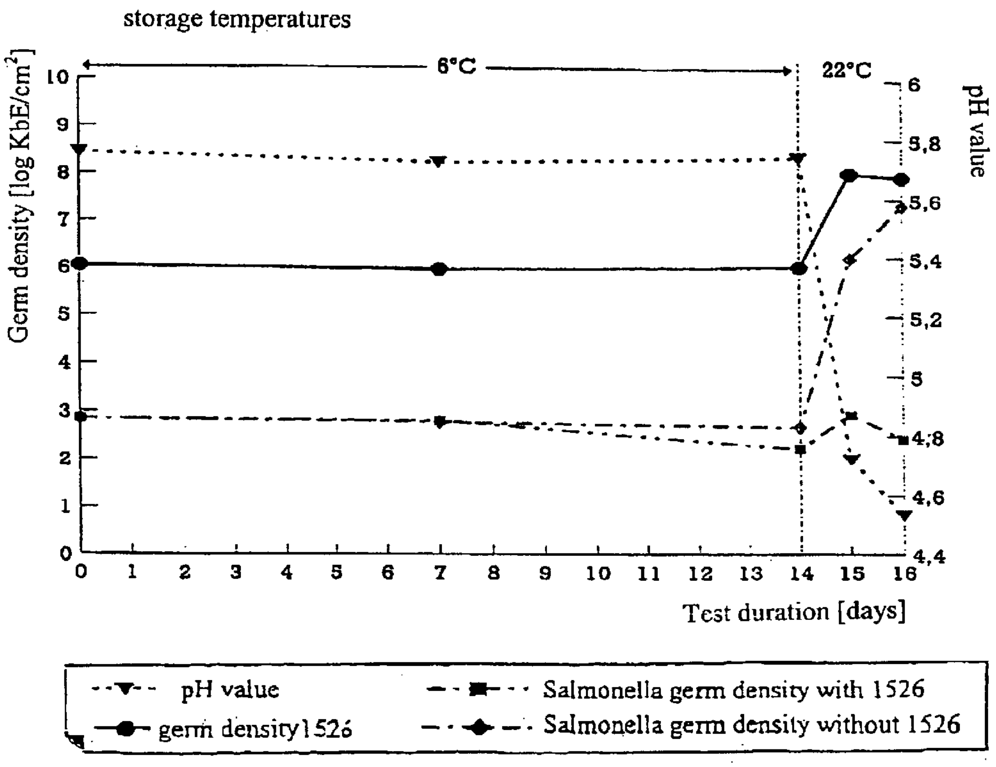

Figure 3: Inhibition of a salmonella pool by *Lactococcus lactis ssp. Lactis 1526* with an inoculation density of 10e5 $KbE/cm^2$ during cold storage (6°C/14 days) and subsequent increase in temperature (22°C/24 hours)
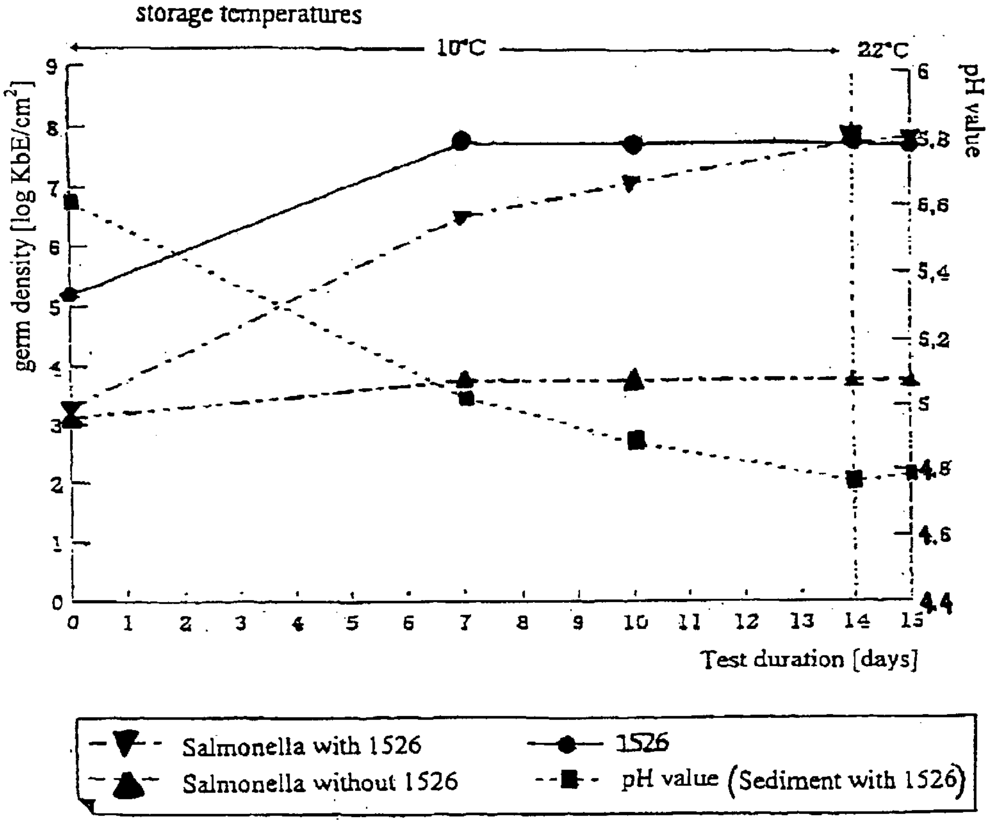

Figure 4: Inhibition of *S. aureus* by *L. Lactis ssp. Lactis 1526* on a sausage sample during cold storage (6°C/6 days) and subsequent increase in temperature (22°C/2 days)
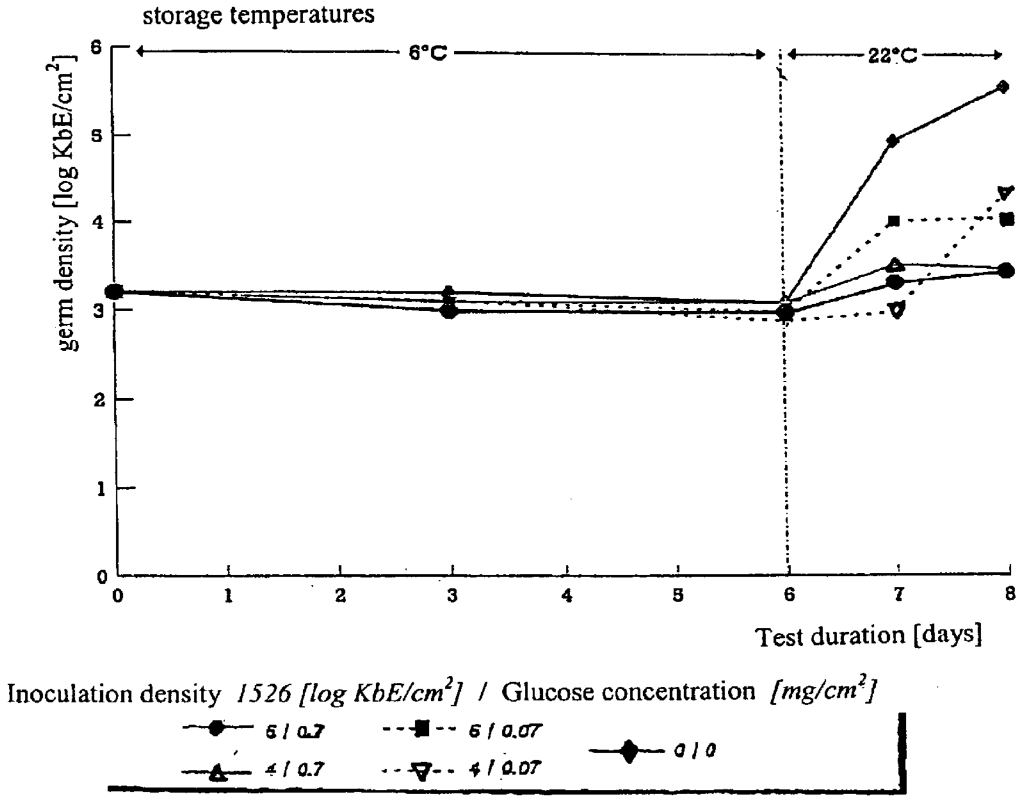

Figure 5: Inhibition of *B. aureus* by *L. lactis ssp. Lactis 1526* on a sausage sample during cold storage (6°C/6 days) and subsequent increase in temperature (22°C/2 days)
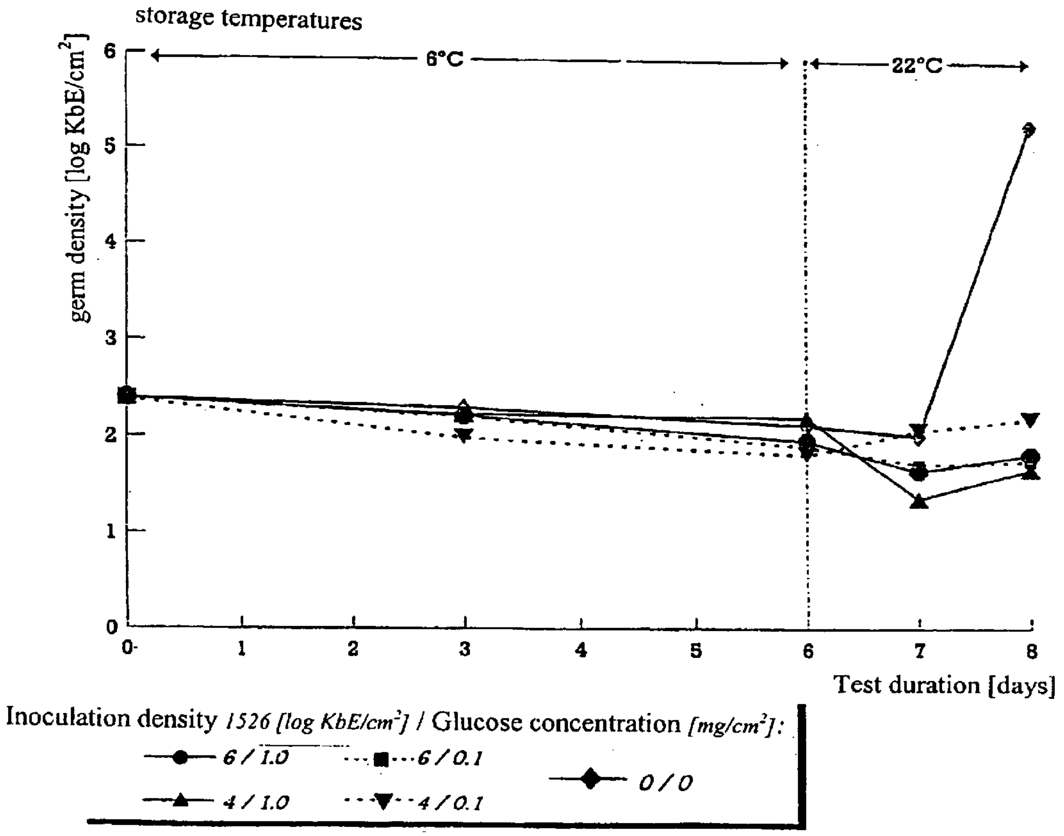

Figure 6: Inhibition of *C. perfringens* by *L. lactis ssp. Lactis 1526* on a sausage sample during cold storage (6°C/6 days) and subsequent increase in temperature (22°C/2days)
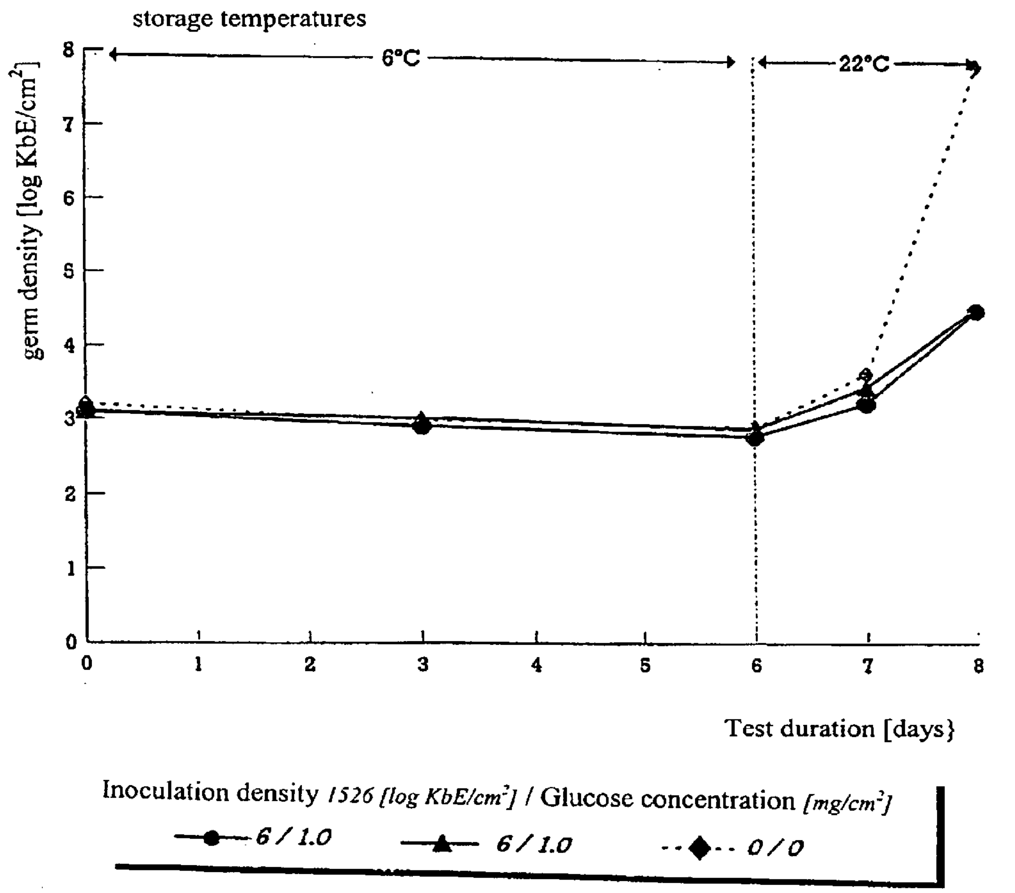

PROTECTIVE CULTURES AND USE THEREOF FOR PRESERVING FOODSTUFFS

The present invention relates to novel protective cultures containing lactic acid bacteria which can be used to preserve food- and feedstuffs which will keep for only a limited period under refrigeration. The protective cultures are able, if the cold chain is interrupted, or the cold temperature is not adhered to, to inhibit the grow of bacteria which are harmful to the consumer.

Certain food- and feedstuff, such as, for example, various meat products, must be stored in a cool place until consumed or prepared by the consumer, i.e. at temperatures below 7° C. to 8° C., so that they remain edible. In the case of this group of food- and feedstuffs which will thus keep for only a limited period under refrigeration, even with careful production practice, the possibility cannot be excluded, that bacteria which are dangerous to the consumer will get into the food- or feedstuff via contaminated raw materials or via a contamination of preliminary product or end product stages.

Bacteria which are dangerous to the consumer, within the meaning of this invention, are bacteria which can produce bacterial food-poisoning. These bacteria include, on the one hand toxinogenic bacteria which can already form toxins in the food- or feedstuff. Consumption of toxin-loaded food- or feedstuff can lead to toxi-infections, e.g. to a disease. On the other hand, bacterial food-poisoning can be caused by toxin-infections bacteria which can multiply in the food- or feedstuff and thus get into the gastrointestinal tract (G. Seidel and J. Kiesewalter: Bacterial Foodstuff Infections and Intoxications. Berlin: Akademie Verlag, 1992).

Most cases of food poisoning caused by bacteria only occur if the pathogens reach relatively high germ densities in the food- or feedstuff consumed (J. Krämer: Foodstuff Microbiology. Stuttgart: Ulmer, 1987). The infection dose (minimum germ-quantity of a pathogen necessary to produce a disease) in food- or feedstuff is generally exceeded if the cold chain is interrupted or the prescribed cool temperature is not maintained. It is especially critical that the infection dose of the toxinogenic and/or toxi-infectious bacteria can be exceeded without producing any sensory change in the food- or feed-stuff that could be detected by the consumer. Therefore agents are desirable which can inhibit the growth of toxinogenic and/or toxi-infectious bacteria in the food- or feedstuff if the cold chain is interrupted or the prescribed cool temperature is not maintained.

An inhibition of growth, i.e. reduction in the growth rate of these dangerous bacteria which would be satisfactory to the consumer has not thus far succeeded in the state of the art, despite a large number of proposals.

It is true that the growth of toxinogenic and/or toxi-infectious bacteria can now be prevented in almost all foodstuffs by means of a large number of chemical additives (see EU Directive No. 95/2/EEC of 20.2.1995) or by physical treatments (application of heat, UV-rays, ionizing rays etc.). However, consumer acceptance of these measures is ever diminishing. The reasons for this are to be found partly in the allergenic potential of many additives. Furthermore, the possibility cannot be excluded that the preservatives are metabolized in the foodstuff or in vivo to produce toxic substances (H-G. Classen, P. S. Elias and W. P. Hammes: Toxicological-hygienic assessment of foodstuff ingredients and additives and serious contaminations; Berlin and Hamburg: Verlag Paul Parey, 1987).

One example of this is the curing of meat products, which involves adding nitrite to the foodstuffs in the form of nitrite curing salt. What is toxicologically questionable in this case is not so much the acute toxicity of the nitrite as the possible formation of carcinogenic nitrosamines in the foodstuff or even in vivo (H. Druckery, R. Preussmann, S. Ivankovic, D. Schmähl,: Organotropic carcinogenic effects in the case of 65 different N-nitroso compounds in BD rats. Krebsforschung 69, 1967, P. 102 ff.). Omission or reduction of the nitrite additive would therefore be extremely desirable. However, in the state of the art there is "no question that not using any curing salts—and not adding any other preservatives that were also not completely safe—would increase the risk of bacterial spoilage of the products and thus jeopardize the consumer's health." (K. Hofmann: Nitrate and its consequences in foodstuffs of animal origin. ADI-Verbraucherdienst 31, 1986, P. 98).

The increasing demand for "natural" and "additive-free" foodstuffs means that, in the case of food- or feedstuffs which will keep for only a limited period just under refrigeration, the growth of toxinogenic and/or toxi-infectious bacteria is frequently only prevented by cooling. If this safety measure is not adhered to, i.e. if the cold chain is interrupted or the necessary cool temperature is not adhered to, the user is exposed to the risk of food poisoning.

This risk could be countered by the use of biological processes. Certain bacteria, including lactic acid bacteria are in principle able to inhibit the growth of other bacteria by the production of a large number of products of metabolism (S. E. Lindgren and W. J. Dobrogosz, FEMS Microbiology Reviews 87:149–173 (1990); H. Asperger, Österreichische Milchwirtschaft 41:1–22 (1986) Attachment 1 to Volume 4).

A use of lactic acid bacteria as protective cultures which is satisfactory for the consumer, i.e. for the inhibition of the growth of toxinogenic and/or toxi-infectious bacteria is however only possible if the bacteria used meet the following strict requirements:

1. A fundamental pre-condition is that of being completely harmless to health, i.e. the bacteria used must have GRAS status (GRAS: Generally Recognised As Safe; see Department of Health and Human Services, Food and Drug Administration, USA "Substances generally recognized as safe; Proposed Rule" (Docket No. 97N-0103), Federal Register Part III; Vol. 62, 1997).
2. The bacteria used must not exhibit any metabolism activities at a cool temperature, which could have a negative sensory effect for the consumer (e.g. souring, influence on colour etc.).
3. Moreover, throughout the period spent in cool storage, potentially metabolically active bacteria must be contained the protective culture in sufficient quantities for the protective culture to be able to inhibit the growth of toxinogenic and/or toxi-infectious bacteria in the case of a rise in temperature, even at the end of the storage period. Potentially metabolically active bacteria are bacteria which exhibit metabolic activity in the case of any rise in temperature.
4. The bacteria used must inhibit the growth of toxinogenic and/or toxi-infectious bacteria within the temperature range of at least 7° C. to 8° C. or above. Even in the case of rapid rises in temperature, as in the case of an interruption to the cold chain, they must for example be able to inhibit bacteria of the family Enterobacteriaceae (e.g. *salmonella*) which multiply very rapidly under these conditions. Moreover, the protective culture used must be able to suppress a broad spectrum of different toxinogenic and/or toxi-infectious bacteria.

The bacteria used up to now in the state of the art to preserve foodstuffs do not meet these requirements:

The inhibiting effect of some of the bacteria used in the state of the art is based on the formation of antagonistic proteins or protein complexes, known as bacteriocins, which are specifically produced by the bacteria to suppress certain other bacteria (Nettles and Barefoot. Journal of Food Protection 6:338 ff, (1993)). These bacteriocins exhibit anti-bacterial activity against closely related species (Tagg et al. (Bacteriological Reviews 40:722–756, 1976)). Thus only a very restricted spectrum of bacteria can be inhibited by the bacteriocins known in the state of the art, mostly limited to gram positive bacteria (L. de Vuyst and E. J. Vandamme: Bacteriocins of Lactic Acid Bacteria.

London, Glasgow, New York, Tokyo, Melbourne, Madras; Blackie Academic & Professional, 1994). The use of bacteriocin-forming cultures is also problematic because bacteriocins frequently lack stability in the foodstuff, are often only produced at low synthesis rates in the foodstuff and because strains resistant to the bacteriocins can occur (F. K. Lücke, Deutsche Milchwirtschaft 16:729 ff., 1994).

Other bacteria used in the state of the art already exhibit metabolic activity during cool storage, i.e. below 7° C. and therefore cannot be used as protective culture within the meaning of this invention (Tanaka, N., et al., Journal of Food Protection 48:697 ff., (1985); Schmidt, U. Fleischwirtsch., 75:24 ff., (1995); Collins-Thompson, D. L. et al., Journal of Food Protection 45:305 ff., (1982); Andersen, L., Fleischwirtsch., 75:705–712 (1995)). Moreover these known bacteria, which have already been examined for use as protective cultures, only exhibit an inhibiting effect towards a few toxinogenic and/or toxi-infectious bacteria and are therefore unable to inhibit a broad spectrum of toxinogenic and/or toxi-infectious bacteria in food- and feedstuffs.

The task of the present invention is therefore to make available protective cultures which can fulfil the abovementioned criteria and whose use in food- and feedstuffs is therefore completely safe. It is a further task of the invention to make available foodstuffs which contain the protective cultures.

To solve the task, novel protective cultures are proposed, which are intended for use in the treatment of food- or feedstuffs. The protective cultures according to the invention contain non-pathogenic, lactic-acid-producing bacteria (lactic acid bacteria) which have the surprising properties of exhibiting no metabolic activity if the cool temperature is adhered to, whereas if the cold chain is interrupted or the cool temperature is not maintained, they can, by the production of products of metabolism, inhibit the growth of a large number of toxinogenic and/or toxi-infectious bacteria. In addition, the number of lactic acid bacteria remains approximately constant in the food- or feedstuffs throughout the storage period, so that, even at the end of the storage, inhibition of the growth of the dangerous bacteria is possible. By use of the protective cultures according to the invention, the consumer can thus be protected against a large number of toxinogenic and/or toxi-infectious bacteria, such as *salmonella*.

Accordingly, the invention relates to protective cultures for the preservation of food- or feedstuffs, which keep for a limited period under refrigeration, these protective cultures being characterized in that they contain non-pathogenic lactic acid bacteria with the following properties:

a) At temperatures below 7° C. to 8° C. the lactic acid bacteria show no perceptible metabolic activity;

b) At temperatures below 7° C. to 8° C. the number of lactic acid bacteria with potential metabolic activity decreases by less than two decimal powers over a period of one to two weeks; and c) At temperatures of at least 7° C. to 8° C. the lactic acid bacteria inhibit the growth of toxinogenic and/or toxi-infectious bacteria According to a preferred embodiment, the protective cultures contain lactic acid bacteria of the genera *Lactococcus, Pediococcus, Lactobacillus, Leuconostoc, Weissella, Bifidobacterium, Enterococcus* and/or *Sporolactobacillus* or mixtures thereof.

According to an especially preferred embodiment, the protective cultures contain lactic acid bacteria of the genera *Lactococcus, Pediococcus, Lactobacillus, Leuconostoc, Enterococcus* or *Weissella,* or mixtures thereof, and according to a particularly preferred embodiment lactic acid bacteria of the genus *Lactococcus.*

According to a further preferred embodiment the protective cultures contain lactic acid bacteria of the species *Lactococcus lactis, Lactococcus garieae, Lactococcus piscium, Lactococcus plantarum* and/or *Lactococcus raffinolactis* or mixtures thereof.

According to an especially preferred embodiment the protective cultures contain lactic acid bacteria of the species *Lactococcus lactis.*

According to a further preferred embodiment the protective cultures contain lactic acid bacteria of the subspecies *Lactococcus lactis* subsp. *cremoris* and/or *Lactococcus lactis* subsp. *lactis* or mixtures thereof. According to a particularly preferred embodiment the protective cultures contain lactic acid bacteria of the species *Lactococcus lactis* subsp. *lactis.*

According to a further preferred embodiment the protective cultures contain lactic acid bacteria of the variants *Lactococcus lactis* subsp. *lactis* var. *diacetylactis.*

According to a particularly preferred embodiment the protective cultures contain lactic acid bacteria of the strain *Lactococcus lactis* subsp. *lactis* 1526. The strain *Lactococcus lactis* subsp. *lactis* 1526 was deposited in accordance with the terms of the Budapest Treaty on the Recognition of the Deposit of Microorganisms for the Purposes of Patent Procedure with the DSMZ Deutsche Sammlung von Mikroorganismen und Zellkulturen GmbH, Mascheroder Weg 1b, D 38124 Brunswick, on Sep. 17, 1998, under number DSM 12415. A confirmation of receipt and viability by the International Depository Authority was issued on Sep. 21, 1998.

According to an especially preferred embodiment the protective cultures according to the invention contain a mixture of the various abovementioned genera, species, subspecies and/or strains.

According to a preferred embodiment the food- or feedstuffs within the meaning of the invention also include preliminary stages such as carcasses or raw materials used in the production of the food- or feedstuffs.

According to a particularly preferred embodiment, the food- or feedstuffs are meat and meat products, fish and fish products, delicatessen salads and meals stored and/or sold pre-cooked. These food- or feed-stuffs include in particular the foods described below.

At temperatures below 7° C. to 8° C., the lactic acid bacteria of the protective cultures according to the invention exhibit no perceptible metabolic activity. Perceptible metabolic activity is taken to mean any metabolic activity that can be detected by the consumer. In particular the lactic acid bacteria exhibit no growth activity, no souring activity, and they produce no products of metabolism which can influence the colour of the food- or feedstuffs.

At temperatures below 7° C. to 8° C., the number of lactic acid bacteria capable of multiplying preferably decreases by less than one decimal power over a period of one to two weeks, and especially preferably by less than one-half of a decimal power.

At temperatures of at least 7° C. to 8° C., the lactic acid bacteria of the protective cultures according to the invention inhibit the growth of the following toxinogenic and/or toxi-infectious bacteria, whilst the invention is not restricted to the inhibition of these bacteria:

*Staphylococcus aureus, Salmonella,* humanpathogenic *E. coli* strains (EIEC, ETEC, EPEC, EHEC), *Shigella, Pseudomonas aeruginosa, Vibrio parahaemolyticus, Aeromonas hydrophila, Camphylobacter jejuni, Bacillus cereus, Clostridium perfingens* and *Clostridium botulinum.*

According to an especially preferred embodiment the growth of the toxinogenic and/or toxi-infectious bacteria is inhibited so that their number does not increase by more than two decimal powers within 48 hours, and preferably by no more than one decimal power.

The lactic acid bacteria of the protective cultures according to the invention inhibit the growth of toxinogenic and/or toxi-infectious bacteria, amongst other things, by production of the following antimicrobially active substances, it being included according to the invention that the lactic acid bacteria can produce some or all of these substances and that the inhibiting potential of the lactic acid bacteria can also be based on other substances: organic acids (lactic acid, acetic acid, formic acid, benzoic acid), diacetyl, carbon dioxide, reducing substances which lead to a drop in the redox potential, hydrogen peroxide, bactericins.

According to a preferred embodiment the lactic acid bacteria inhibit the growth of toxinogenic and/or toxi-infectious bacteria by the production of organic acids, preferably lactic acid.

According an especially preferred embodiment, at temperatures of at least 7° C. to 8° C. or above, the lactic acid bacteria of the protective cultures exhibit a perceptible metabolic activity, preferably a souring of the food- or feedstuff.

According to a particularly preferred embodiment, the temperature below which no metabolic activity of the lactic acid bacteria of the protective cultures according to the invention takes place and above which the lactic acid bacteria can inhibit the growth of toxinogenic and/or toxi-infectious bacteria is 7° C.

The lactic acid bacteria of the protective cultures according to the invention can be obtained by the following method:

1. Firstly, lactic acid bacteria are isolated, which are to be classified by one of the abovementioned genera, species and/or strains or mixtures thereof. These are preferably isolated out of the food- and feedstuffs, in which the lactic acid bacteria are later to be used. This ensures optimum adaptation to the food- or feedstuff, for example with regard to growth, nutrient exploitation or lactic acid production.

Methods of isolating lactic acid bacteria are known in the state of the art (J. Baumgart, W. in Heeschen (Hrsg.): Handbook of Food Hygiene. Hamburg: Behr's, 1 ff., (1994), especially Chapter 4, p. 216 ff.). This also describes methods whereby it can be examined whether the bacteria isolated are in fact lactic acid bacteria.

2. The growth behaviour and the metabolic activity are then examined at a temperature below 7° C. to 8° C. and above. Below 7° C. to 8° C. the bacteria must exhibit no perceptible metabolic activity, especially no souring activity. At temperatures of at least 7° C. to 8° C. or above the bacteria must exhibit perceptible metabolic activity, especially souring activity.

It is further examined whether the number of isolated lactic acid bacteria capable of multiplying decreases by less than two decimal powers at a temperature below 7° C. to 8° C. over a period of one to two weeks in a food- or feedstuff to which these lactic acid bacteria have been added. For this purpose a specific quantity of bacteria, preferably $10^7$ bacteria/$cm^2$ surface of the food- or feedstuff, is incubated together with the food- or feedstuff for one to two weeks. The number of bacteria is then determined using a method known to the expert (J. Baumgart, loc. cit., Chapter 5, p. 74 ff.).

To this characterization a precise characterization of the isolated lactic acid bacteria can preferably be added. There is a whole series of methods available for this purpose, for example biochemical identification using the miniaturized "api 50 CHL" culture mediums with indicator stains (bioMerieux, Marcy-l'Etoile, France) or analysis of the 165 rDNA sequences (B. Pot et al.: Modern methods used for identifiation and classification of lactic acid bacteria; in: L. de Vuyst and E. J. Vandamme: Bacteriocins of Lactic Acid Bacteria. London, Glasgow, New York, Tokyo, Melbourne, Madras: Blackie Academic & Professional 1991; Chapter 2.3, P. 40 ff.).

3. It must then be examined whether the isolated lactic acid bacteria are able to inhibit the growth of toxinogenic and/or toxi-infectious germs in food- or feedstuffs. For this purpose the toxinogenic and/or toxi-infectious bacteria in the food- or feedstuffs are incubated together with the isolated lactic acid bacteria (see also Example 8). The incubation preferably takes place at temperatures below 7° C. to 8° C. and then at temperatures of at least 7° C. to 8° C. or above. Growth inhibition results if, during the incubation of toxinogenic and/or toxi-infectious bacteria together with the isolated lactic acid bacteria, the toxinogenic and/or toxi-infectious bacteria grow more slowly than during incubation of toxinogenic and/or toxi-infectious bacteria without addition of the isolated lactic acid bacteria.

A further object of the invention is lactic acid bacteria belonging to the strain *Lactococcus lactis* subsp. *lactis* 1526 (DSM 12415, see above). This strain has the surprising property of exhibiting no perceptible metabolic activity at temperatures below 7° C. to 8° C., whilst at temperatures of at least 7° C. to 8° C. it can inhibit the growth of toxinogenic and/or toxi-infectious bacteria. It also has the surprising property, that, at temperatures below 7° C. to 8° C., the number of potentially metabolically active lactic acid bacteria of the strain in the food- or feedstuff in question decreases by less than two decimal powers over a period of one to two weeks.

A further object of the invention is the use of the protective cultures according to the invention for the preservation of food- and feed-stuffs, which can be kept under refrigeration for a limited period. This involves treating the food- and feed-stuffs with the protective cultures according to the invention, by bringing the food- or feedstuffs into contact with the protective cultures so that the protective cultures are able to inhibit the growth of toxinogenic and/or toxi-infectious bacteria.

According to a preferred embodiment the food- or feedstuffs are treated with the protective cultures according to the invention, by applying the protective cultures to the surface of the products, preferably by spraying or rubbing in. According to a further embodiment the products are treated with the protective cultures, by mixing and/or stirring the protective cultures into the product.

According to a preferred embodiment, the food- or feedstuffs are treated with a powder containing the protective cultures and, possibly, suitable carriers. Suitable carriers include, for example, saccharides, preferably mono- or disaccharides.

According to a further preferred embodiment, the food- or feedstuffs are treated with a liquid medium containing the protective cultures. The liquid medium must be formulated in such a way that it guarantees the viability of the culture during the treatment.

According to an especially preferred embodiment the liquid medium is an aqueous medium such as physiological common salt solution or drinking water.

According to a preferred embodiment the food- or feedstuffs are treated with a lactic acid bacteria quantity of $10^4$ to $10^8$ lactic acid bacteria per g or ml or $cm^2$ surface of the food- or feedstuff, preferably with a lactic acid bacteria quantity of $10^5$ to $10^6$ lactic acid bacteria per g or ml or $cm^2$ surface.

Preferably, during the treatment, a source of carbon, preferably carbohydrates, especially preferably glucose, saccharose or lactose is added to the food- or feedstuffs.

According to a preferred embodiment, the protective cultures according to the invention, with which the food- or feedstuffs are treated, represent a mixture of the abovementioned genera, species, subspecies and/or strains.

A further object of the invention is a food- or feedstuff, characterized in that it contains the protective cultures according to the invention. For this purpose the food- or feedstuff is treated with the protective cultures according to the embodiments described above.

According to a preferred embodiment, the food- or feedstuff is selected from the group of meat or meat products, particularly preferably from the group comprising:

- portioned fresh meat, offal, poultry and pieces of poultry, which are treated by applying the protective cultures according to the invention to the surface;
- carcasses, parts thereof, de-boned parts thereof, sliced cold meat products such as sliced sausage, cooked sliced sausage, sliced cooked or raw cured products, which are treated by application of the protective cultures according to the invention;
- chopped meat products such as for example mince (minced steak, chopped steak, steak tartar, minced beef, minced pork, chopped pork), mince preparations, bratwurst products, which are treated by stirring in, or applying the protective cultures according to the invention to the surface.

According to a further especially preferred embodiment, the food- or feedstuff is selected from the group of fish and fish products, particularly preferably from the group consisting of fresh fish (fish fillets, fish steaks), smoked fish, such as cold sliced products, or molluscs and crustaceans, which are in each case treated or applying the protective cultures according to the invention to the surface.

According to a further especially preferred embodiment, the foodstuffs are delicatessen salads. Especially preferred are foodstuffs from the group consisting of salads based on meat, fish, molluscs, crustaceans and vegetables or salads with pasta, and, according to an especially preferred embodiment, the delicatessen salads are produced with a basis of mayonnaise, salad-mayonnaise or remoulade, in each case with the delicatessen salads being treated by mixing/stirring in of the protective cultures according to the invention, or by application of the protective cultures according to the invention to the surface.

According to a further especially preferred embodiment, the foodstuffs are pre-cooked ready meals. Pre-cooked ready meals within the meaning of the invention are meals which are stored and/or sold already cooked. These meals are treated by mixing/stirring in of the protective cultures according to the invention, or by application of the protective cultures according to the invention to the surface.

According to a further especially preferred embodiment, the foodstuffs are selected from the group of dairy products, particularly preferably from the group consisting of fresh milk, yoghurt, quark and cheese.

The present invention thus for the first time makes available protective cultures which inhibit the growth of toxinogenic and/or toxi-infectious bacteria at temperatures of at least 7° C. to 8° C. or above, whilst exhibiting no perceptible metabolic activity at temperatures below 7° C. to 8° C. The protective cultures according to the invention can be used directly in food- or feedstuffs intended for human or animal use, which will keep for a limited period under refrigeration only, as they are not pathogenic for the consumer.

The invention is explained below using figures, tables, and examples.

DESCRIPTION OF THE FIGURES

FIG. 1 Behaviour of *Lactococcus lactis* subsp. *lactis* 1526 in vacuum-packed sliced sausage during 3 weeks' cold storage (6° C.) and a subsequent simulated interruption of the cold chain (48 h/22° C.). The germ density (log KbE/$cm^2$) of *L. lactis* subsp. *lactis* 1526 is represented along the left-hand y-axis, whilst the pH value in the sausage during the experiment is shown by the right-hand y-axis. The duration of the test is shown by the x-axis. The sliced sausage was vacuum-packed, the covering film consisted of OPP/$SIO_x$/PE. In the case of irradiated samples, the samples were irradiated at 1300 lux, with a distance of 40 cm between vacuum-packed samples and fluorescent tubes.

FIG. 2 Inhibition of the *salmonella* pool during a simulated interruption of the cold chain (22° C./48 h) by *L. lactis* subsp. *lactis* 1526. The y-axis shows the germ density of the bacteria, whilst the x-axis shows the duration of the experiment.

FIG. 3 Inhibition of the *salmonella* pool during inadequate cold storage (10° C.) and a subsequent simulated interruption of the cold chain (22° C.) by *Lactococcus lactis* subsp. *lactis* 1526. The y-axis shows the germ density of the bacteria, whilst the x-axis shows the duration of the experiment.

FIG. 4 Inhibition of *Staphylococcus aureus* subsp. *aureus* during a simulated interruption of the cold chain (22° C./48 h) by *Lactococcus lactis* subsp. *lactis* 1526. The inhibiting activity is indicated dependent on the inoculation density of the protective culture and the quantity of glucose added. The y-axis designates the germ density of the staphyolococci, whilst the x-axis indicates the duration of the experiment.

FIG. 5 Inhibition of *Bacillus cereus* during a simulated interruption of the cold chain (22° C./48 h) by *L. lactis* subsp. *lactis* 1526. The inhibiting activity is indicated dependent on the inoculation density of the protective culture and the quantity of glucose added. The y-axis designates the germ density of *Bacillus cereus,* whilst the x-axis indicates the duration of the experiment.

FIG. 6 Inhibition of *Clostridium perfringens* during a simulated interruption of the cold chain (22° C./48 h) by *L. lactis* subsp. *lactis* 1526. The inhibiting activity is indicated dependent on the inoculation density of the protective culture and the quantity of glucose added. The y-axis designates the germ density of the clostridia, whilst the x-axis indicates the duration of the experiment.

EXAMPLES

Example 1

Isolation of Lactic Acid Bacteria Strains from Foodstuffs

To start a strain collection, lactic acid bacteria were isolated predominantly from meat products. This was to guarantee that the isolated lactic acid bacteria were organisms adapted to the substrate "meat". It was a further requirement that the isolates could prevail over a competing flora. The meat products were therefore stored at 30° C. for 48 h before the isolation. Thus the lactic acid bacteria flora was able to prevail, the dominant lactic acid bacteria reached high germ densities in the samples.

In the case of loose-packed samples which were also used in addition to the vacuum-packed products, the germs were exclusively isolated from parts that were separated, sterile, from the inside of the test samples.

The test pieces, weighing approx. 5 to 10 g, were placed in 90 ml sterile Ringer's solution (Unipath GmbH, D-46467 Wesel, BR 52) and according to their composition, pulverized and for two minutes at 13500 RPM with an Ultra-Turrax (T 225, JANKE & KUNKEL/Staufen) or for ten minutes in the Stomacher (LabBlender 400, SEWARD-MEDICAL/London) and suspended. From the suspension thus produced, continuous series of dilutions were produced, in each case in 9 ml of sterile Ringer's solution. From the dilution stages $10^{-4}$–$10^{-8}$, in each case 100 μl are spread out on Chalmers (modified) and on MRS culture media (for culture media see Table 2). The incubation took place at 30° C. in anaerobic pots (Unipath, HP 11), in which an anaerobic atmosphere was produced using AnaeroGen (Unipath, AN 35)

After 3 to 4 days a maximum of five colonies per product were removed from the culture media, differing on the basis of their macroscopic morphology. In the case of the Chalmers culture media, special consideration was given to those colonies characterized by a high halo diameter (decolorized, clear). This can be judged a sign of strong acid formation. The cultures removed were suspended in 5 ml of a MRS broth and incubated anaerobically at 30° C. for 48 hours. If, after the two days' incubation a distinct clouding appeared, a dilution smear was applied to Chalmers and MRS. After corresponding incubation (4 days/30° C./anaerobic) individual colonies were removed and the pure culture thus produced again cultivated in a MRS broth. The isolates were placed in the strain collection as frozen preparations. To produce a preparation, the freshly cultivated pure cultures are spread out on a MRS culture medium and incubated in accordance with the conditions already described. After 4 to 5 days the bacteria coating was rinsed off with 1.5 ml of a caseine peptone-soymeal peptone solution USP (Unipath, CM 129) and introduced into 6 ml of a sterile skimmed milk solutiion (Unipath, L 31). After mixing the bacteria suspension was placed in culture tubes and stored deep-frozen at −20° C.

Example 2

Classification of the Isolated Lactic Acid Bacteria Strains Based on General Characteristics The isolates included in the strain collection were roughly classified on the basis of gram-reaction, catalase and oxidation-fermentation tests, with regard to growth behaviour on corresponding culture media (MRS, Chalmers, Rogosa) and also on the basis of a microscopic and macroscopic assessment of their morphology. A positive gram reaction, a negative catalase test, fermentative carbohydrate breakdown and the colony morphology on a modified Chalmers culture medium (halo formation by acid) are regarded as general characteristics making it likely that the isolates belong to the group of lactic acid bacteria (Baumgart, J. et al., loc. cit., Chapter 4.8, p. 245 ff.). A formation of gas from glucose in the OF test, the microscopic image and the growth behaviour on a Rogosa culture medium may, on the other hand, already provide indications of belonging to a certain genus (Baumgart, J. et al., loc. cit., Chapter 4.8, p. 245 ff.).

Gram Reaction

Gram coloration was carried out on freshly cultivated cultures (surface colonies). The ColorGram 2 test kit was used for the coloration (bioMérieux/Marcy-l'Etoile, France). To check the coloration behaviour in each case, a gram-positive (*Bacillus subtilis*) and a gram-negative (*Eschericia coli*) culture were treated at the same time.

Catalase Test

Surface colonies of the isolate to be tested were removed with a diluting loop and smeared onto a slide with a 3% $H_2O_2$ solution (Bactident Catalase, Merck, 11351). The presence of catalase is indicated by a formation of gas.

Oxidation-Fermentation Test

The OF test according to Hugh, R. and Leifson, E., J. Bact., 66: 24 ff. (1953) is used to check whether the bacteria isolate utilizes glucose fermentatively with formation of acid and possibly gas. A carbohydrate-free OF-base culture medium (Merck, 10282) is used as a test medium, to which a 10% sterile-filtered glucose solution is added after autoclaving (100 ml to 1 l culture medium). The pure culture, removed with an inoculating needle was in each case inoculated into two tubes, filled with the culture medium in parallel with the stabbing process. One of the two tubes was overlaid with a finger's breadth of sterile paraffin oil after the inoculation, to keep oxygen out. After an incubation of 2–4 days at 37° C., in the case of a fermentative glucose utilization, a colour change was observed using the bromo thymol blue indicator in both tubes. In addition, during assessment, any gas formation (bubbles and/or gaps in the culture medium column) and any mobility (culture medium swarmed through) is taken into account.

Biochemical Identification of the Isolates

The biochemical identification of the isolates classified as lactic acid bacteria was carried out using the miniaturized "api 50 CHL" culture mediums with indicator stains (bioMerieux, Marcy-l'Etoile, France). In the api 50 CHL system, metabolism is examined using 49 carbohydrates. The resultant biochemical profile is interpreted with the APILAB Plus software which is available for this purpose.

The isolates to be identified were cultivated out of a frozen culture in an MRS broth, centrifuged off and then placed in Ringer's solution. The inoculum required for the tests was adjusted using McFarland Standard 2.0 (bioMérieux, 70900). The micro-tubes of the test strips were inoculated with 100 μl of the germ suspension, overlaid with sterile paraffin oil and incubated in a humid chamber at 30° C. Evaluation of the micro-tubes was carried out after 24 and 48 h, when a bromo-cresol purple indicator change caused by fermentation was judged positive.

Example 3

Determination of Growth and Souring Activity of the Isolated Lactic Acid Bacteria Strains.

Recording of the growth behaviour of the lactic acid bacteria isolates was carried out using the method of Reuter, G., Archiv für Lebensmittelhygiene, 12: 257 ff. (1970). A MRS broth was used as culture medium, with 10 ml being placed in test tubes in each case. The culture solutions were then inoculated with $10^5$ germs in each case. The temperatures tested were 6° C., 10° C. and 15° C., with the incubation period being adapted to the temperature in question. The samples stored at 6° C. were assessed after 14 days, the 10° C. samples after 7 days, and the 15° C. samples after 5 days. After the two-week test period the samples stored at 6° C. were incubated at 22° C. for 24 hours, to determine whether the culture still had sufficient vitality after refrigeration.

After the corresponding test periods, a multiplying of germs was ascertained on the basis of a clouding of the broth or on the basis of a sediment. Moreover, the pH value of the culture solution was determined, to detect the souring activities of the isolates. Cultures showing no growth/souring at 6° C. were judged as positive. On the other hand, at 15° C. distinct multiplying must occur, and the pH value of the culture solution must be below 5.0.

Example 4

Characterization of the Lactic Acid Bacteria Culture *L. lactis* Subsp. *lactis* 1526

The lactic acid bacteria culture with the strain designation *Lactococcus lactis* subsp. *lactis* 1526 was isolated from a vacuum-packed sliced sausage, from Hong Kong, in accordance with Examples 1 and 3. The surface growth of the culture at 30° C. under anaerobic conditions could be designated as good, on the culture media according to de Man, Rogosa and Sharpe (MRS) and on a culture medium according to Chalmers (modified). On a MRS culture medium, after three days' incubation at 30° C., the culture showed smooth, round colonies with a halo diameter>1 mm. On a culture medium according to Chalmers, colonies formed which are distinguished above all by a pronounced halo formation, indicated strong acid formation. Growth on a Rogosa culture medium, which was exposed to a selective isolation of lactobacilli was, in contrast, only very weak.

The microscopic morphology varies greatly with different culture conditions. The description varies from "coccoid" to "short rod", with both forms possibly appearing in one preparation. The germs are predominantly present in chains, and sometimes in pairs. The culture shows excellent vitality when cultivated according to the freeze-culture process. Germ densities of more than 109 KbE/ml were achieved in the culture broth (MRS broth) after 24 hours at 30° C.

Biochemical identification using the api 50 CH rapid test from bioMerieux produced the species "*Lactococcus lactis* subsp. *lactis*" as taxon of first choice, with 98.4% identification. DNA sequencing carried out by the Deutsche Sammlung von Mikroorganismen und Zellkulturen GmbH in Brunswick confirmed the biochemical identification. Examination of the 16S rDNA sequence similarity with the sequencing of the range with the greatest variability resulted in 99.8% agreement with *Lactococcus lactis* subsp. *lactis*. The end product of the glucose fermentation is lactic acid with an L(+)-configuration. Lactate can be formed from, amongst other things, glucose, fructose, mannose and lactose, as well as ribose, trehalose and saccharose.

Example 5

Determination of Germ Densities

The germ densities were determined according to the method described by J. Baumgart, W. in Heeschen, (Hrsg): Handbook of food hygiene. Hamburg: Behr's 1 ff., (1994). The sample to be tested (20 g) was weighed with 80 ml sterile Ringer's solution in a stomacher bag on a platform-type balance. Homogenization was carried out with a bag-pressing device (Stomacher 400). The homogenization time at the average running speed, contrary to Baumgart's recommendation, amounted to 10 min., as the homogenization times of a maximum of 60 s proposed in the literature proved insufficient with the foodstuff to be examined.

From the homogenized sample, 1 ml was removed and pipetted into 9 ml Ringer's solution. The total number of decimal dilutions of a sample was based on the number of germs to be expected. From the individual dilution stages, either 100 μl were removed for a surface culture, or 1 ml for a pouring culture and spread onto the corresponding culture media according to the relevant method, or mixed with the culture medium which was still liquid. The culture media used for the individual groups of germs and the corresponding incubation conditions are listed in Examples 6 and 7.

For each germ-number determination at least 2 samples are used, each being subjected to two series of dilutions. From the numbers of germs ascertained for each test sediments the germ density was determined via the arithmetic average. The repeat tests were staggered in time, with different sample charges being used for the tests. If the same test sediments resulted in a difference in germ densities in excess of log 1 ($|\log KbE_{Test1} - \log KbE_{Test\,2}| > 1$), the test had to be repeated.

Example 6

Cultivation of Germs Presenting a Risk to Hygiene

The cultivation of freeze-cultured germs presenting a risk to hygiene took place over 24 h, in each case in 100 ml caseine peptone-soymeal peptone solution USP (Unipath, CM 129). *Bacillus cereus* and *Clostridium botulinum* were incubated at 30°, *Staphylococcus aureus, Clostridium prefringens* and the individual strains of *salmonella* at 37°. The cultivation of *C. perfringens* took place under anaerobic conditions.

The methods used, the methodology and the incubation conditions for germ number determination of the test germs used as germs presenting a risk to hygiene are shown in Table 1.

Table 1 (See P. 27)

Example 7

Cultivation of Lactic Acid Bacteria Strains

The strains of lactic acid bacteria classified as positive in Examples 1 to 3 were cultivated at the start of the test, in each case for 24 h at 30° in 10 ml MRS broth (Unipath, CM 359). After cold storage at 6° for a maximum of 10 days, 100 μl bacteria suspension was removed from the culture broth and introduced into 10 ml MRS culture solution for new cultivation. After the 2nd cultivation (30°/24 h) the bacteria mass was centrifuged off at 8,000 RPM for 10 min. (Biofuge 28 RS, HERAEUS SEPATECH/Osterode). The supernatant was poured off and the sediment suspended with the same quantity of sterile Ringer's solution. The cell suspension was again centrifuged under the same conditions, the supernatant removed and again replaced by the same quantity of sterile Ringer's solution. The cultures thus purified were stored under refrigeration (6°, max. 7 days) until used, and added to the sausage samples after determination of the germ density.

To determine the germ density and/or detect the germs, a modified Chalmers culture medium was used. Pouring cultures were settled from the corresponding dilutions, and incubated for 3–5 days at 30° C.

TABLE 1

(to Example 6)

| Test micro-organisms | Medium | Method | Incubation conditions (Temperature/Time/Atmosphere) |
| --- | --- | --- | --- |
| *Staphylococcus aureus* (DSM 346) | Baird-Parker culture medium | Pouring plate method | 37° C./24–48 h/aerobic |
| *Salmonella*[1)] | Gassner culture medium/brilliant green phenol-lactose-saccharose-agar. mod. | Spatula method | 37° C./24–48 h/aerobic |
| *Bacillus cereus* (DSM 31) | *Bacillus cereus* selective culture medium | Spatula method | 37° C./24–48 h/aerobic |
| *Clostridium perfringens* (DSM 756 Type A) | OPSP selective culture medium | Pouring plate method | 37° C./18–24 h/anaerobic |

[1)]The following *salmonella* from the National Reference Centre for Salmonelloses were used: *Salmonella enteritidis* (Se 125/94 Lysotype 8/7, Se 203/94 Lysotype 8/7, Se 315/94 Lysotype 4/6), *Salmonella panama* (SZ 1107/93, SZ 1249/93, SZ 2365/93), *Salmonella typhimurium* (SZ 218/94, SZ 235/94, SZ 284/94)

TABLE 2

| Medium | Intended use | Manufacturer/Article no. |
| --- | --- | --- |
| Caseine peptone-soymeal peptone solution | Enrichment/culture of test microorganisms | Unipath/CM 129 |
| MRS broth | Enrichment/culture of lactic acid bacteria | Unipath/CM 359 |
| MRS culture medium | Colony-number determination of lactic acid bacteria | Unipath/CM 361 |
| Culture medium according to Chalmers, modified | Colony-number determination of lactic acid bacteria | " |
| Rogosa culture medium | Isolation and colony-number determination of *lactobacilli* | Unipath/CM 627 |
| Plate-count culture medium | Determination of total mesophilic germ number | Merck/5463 |
| Yeast and mould agar[1] | Colony-number determination of yeasts and moulds | Unipath/CM 920 |
| *Pseudomonas* selective culture medium | Selective isolation of *Pseudomonas* spp. | Unipath/CM 559 + SR 103 |
| Gassner culture medium | Detection and isolation of *Enterobacteriocene*, colony-number determination of *Salmonella enterica* | Unipath/CM 431 |
| Baird-Parker culture medium | Colony-number determination of *Staphylococcus aureus* | Unipath/CM 275 + SR 54 |
| *Bacillus cereus* selective culture medium | Isolation and colony-number determination of *Bacillus cereus* | Unipath/CM 617 + SR 99 |
| RCM agar | Colony-number determination of *clostridia* and other anaerobes, colony-number determination of *C. botulinum* | Unipath/CM 151 |
| OPSP selective culture medium | Isolation and colony-number determination of *Clostridium perfringens* | Unipath/CM 543 + SR 76 + SR 77 |
| Brilliant green phenol red lactose saccharose agar, modified | Colony-number determination of *Salmonella enterica* | Unipath/CM 329 + SR 87 |

[1]Culture medium according to Chalmers, modified

For colony-number determination of lactic acid bacteria, the selective culture medium according to Chalmers was used, in a modified composition according to Vanos V. and Cox L. Food Microbiol. 3: 233 ff. (1986):

| | | |
| --- | --- | --- |
| Lactose | 20.0 g | After autoclaving (121.1° C./15 min) 1 ml sterile-filtered polymixin-B-sulphate (Unipath) is added to the culture medium cooled to ca. 45° C. |
| Glucose | 20.0 g | |
| Soya-peptone | 3.0 g | |
| Meat extract | 3.0 g | |
| Calcium carbonate | 20.0 g | |
| Agar | 15.0 g | |
| Neutral red | 0.5 ml (1%) | |
| Aqua dest. | ad 1.0 l | |

[2)]The selectivity of the culture medium was increased by souring with 10% lactic acid solution (UNIPATH SR21) to a pH value of 4.0.

Example 8

Inhibition of Toxinogenic and/or Toxi-Infectious Germs in Vacuum-Packed Sliced Sausage by *Lactococcus lactis* Subsp. *lactis* 1526

The most important requirement of a protective culture is the hygienic safeguarding of a foodstuff when not refrigerated correctly. Thus the bacteria used according to the invention must act sufficiently antagonistically against toxinogenic and/or toxi-infectious bacteria, and therefore clearly suppress any multiplying and/or toxin formation. The result of the tests described in Examples 1 to 4 show that bacteria belonging to the strain *Lactococcus lactis* subsp. *lactis* 1526 were able to assume this function. In the following tests, it should therefore be clarified, whether the antagonistic effect can also be achieved on the cut surface of a sausage. The sausages were produced by a process known in the state of the art (Literature on the production of sausages: A. Fischer:

Product-related Technology—Manufacture of Meat Products in: O. Prǎndl, A. Fischer, T. Schmidhofer, H.-J. Sinell (HRSG.): Meat—Technology and Hygiene in Production and Processing. Stuttgart: Ulmer, 1988, P. 505 ff.).

The tests were carried out under practical conditions. To simulate a smear infection, the suspensions with the pathogenic germs were spread with a spatula after application to the cut surface. Contamination of the sausage via the slicing machine, as referred to in the literature (Schmidt, U. and Gardill, E., Annual Report of the Federal Research Institute for Meat Research, S.C. 25 (1986) led to very uneven distribution, with the blade already scraping a majority of the germs off, especially at the edge, which resulted in the detection of some relatively large areas (>1 $cm^2$), in which no test germs appeared.

The protective culture was then applied via a spraying nozzle using compressed air. Spraying of the germ suspensions led to an even distribution of germs over the surface. Only an even distribution of the protective culture can have the optimum inhibiting effect on the whole surface. To prevent some of the pathogenic germs from adhering to the packaging film and thus not being detected, a further slice of sausage was in each case placed on top of the contaminated slice. The samples were subsequently vacuum-packed and stored at the corresponding temperatures. As the surface was decisively important for the microbiological tests, the germ densities were indicated in the following tests relative to the surface [KbE/$cm^2$].

FIG. 1 shows the behaviour of *Lactococcus lactis* subsp. *lactis* 1526 in vacuum-packed sliced sausage during three weeks' cold storage at 6° C. and a subsequent simulated interruption to the cold chain (48 h /22° C.).

A) Inhibition of the *Salmonella* Pool

*Salmonella* multiply very rapidly if the necessary cold temperatures are not maintained. The screening of the lactic acid bacteria isolates was therefore especially geared to their antagonistic effect against *salmonella*. The dependence of inhibition of the C-source concentration and the sowing density of the protective culture were examined in vacuum-packed sliced sausage, by establishing the inhibiting effect of *L. lactis* subsp. *lactis* 1526 on a *salmonella* pool (consisting of 9 wild strains, see Table 1) with various inoculation densities of the lactic acid bacteria culture and at various glucose concentrations.

The uncured sausage samples were "smear-infected" with a total of $4.4\times10^4$ *salmonella*, with examination of the inoculation density showing a recovery rate of 70%, corresponding to an actual *salmonella* density of 700 KbE/$cm^2$. *Lactococcus lactis* subsp. *lactis* 1526 was then sprayed on in a density of $10^6$ KbE/$cm^2$. A glucose quantity of 0.7 mg/$cm^2$ was sprayed onto the surface over the protective culture suspension. The desired lactococci density of $10^6$ KbE/$cm^2$ was approximately achieved ($1.1\times10^6$ KbE/$cm^2$). The sprayed slices were covered with a further slice and vacuum-packed. The samples were then stored in a cool incubator at 6° C. After 14 days the temperature was increased to 22° C., to simulate an interruption to the cold chain.

During cold storage at 6° C. the germ densities of the *salmonella* and the protective culture and the pH value changed only slightly (FIG. 2). After the temperature was increased to 22° C., there was, as expected, an increase in the numbers of *salmonella* germs in the samples without the protective culture. In contrast, the samples with the protective culture were distinctly soured. Already after 24 hours, a surface pH value of 4.72 was measured. The *salmonella* were very clearly inhibited by this. During the first 24 hours there was only a slight increase in the cell numbers from 170 to 900 KbE/$cm^2$. After a further 24 hours, an average of 270 KbE/$cm^2$ could still be detected. Thus the germ number level was below the inoculation density of 700 KbE/$cm^2$ (see FIG. 2).

The tests described so far were carried out at a temperature of 22° C., to simulate an interruption to the cold chain. A microbial hygiene risk can however also occur, if the required cool temperature of 7° C. is exceeded. Therefore further investigations were carried out at a temperature of 10° C. In these tests the desired inoculation density of the *salmonella* amounted to $10^3$/$cm^2$; the density actually found was $1.36\times10^3$ KbE/$cm^2$. The lactococci were inoculated with germ densities of $10^3$ KbE/$cm^2$ (FIG. 3). In addition, 0.7 mg/$cm^2$ glucose was applied.

FIG. 3 shows the souring activity of the protective culture and the growth behaviour of the *salmonella* in the samples with and without added protective culture. The *salmonella* population without the protective culture was able to multiply rapidly. In the samples with the protective culture, *Lactococcus lactis* subsp. *lactis* 1526 already reached the maximum germ number of $5.9\times10^7$ KbE/$cm^2$ on the 7th day; in the further course of the test the numbers of cells decreased slightly. During the first week the pH value clearly dropped. On the 7th day average values of 5.02 were measured on the surface, and after 14 days values of 4.76 were achieved. In the presence of the protective culture the *salmonella* were only able to multiply weakly whilst stored at 10° C. On the 14th day *salmonella* germ numbers of only $6.1\times10^3$ KbE/$cm^2$ were determined. After 14 days' storage the temperature was increased to 22° C. However the *salmonella* were no longer able to multiply due to the dominance of the lactococci.

B) Inhibition of *Staphylococcus aureus*

Tests to investigate the antagonistic effect of *L. lactis* subsp. *lactis* 1526 towards *Staphylococcus aureus* were carried out in accordance with the method described for the tests described under A) with *salmonella*. The results of the test are shown in FIG. 4. FIG. 4 clearly shows that *L. lactis* subsp. *lactis* 1526 is able to considerably reduce the growth of *Staphylococcus aureus* if refrigeration is interrupted.

C) Inhibition of *Bacillus cereus*

Tests to investigate the antagonistic effect of *L. lactis* subsp. *lactis* 1526 towards Bacillus cereus were carried out in accordance with the method described for the tests described under A) with *salmonella*. The results of the test are shown in FIG. 5. FIG. 5 clearly shows that *L. lactis* subsp. *lactis* 1526 is able to completely prevent the growth of *Bacillus cereus* if refrigeration is interrupted.

D) Inhibition of *Clostridium perfringens*

Tests to investigate the antagonistic effect of *L. lactis* subsp. *lactis* 1526 towards *Clostridium perfringens* were carried out in accordance with the method described for the tests described under A) with *salmonella*. In addition 0.5% glucono-delta-lacton (W/V) was added to the protective culture. The results of the test are shown in FIG. 6. It is clear that, in the presence of glucono-delta-lacton, *L. lactis* subsp:. *lactis* 1526 is able to prevent the growth of *C. perfringens* if refrigeration is interrupted.

What is claimed is:

1. Isolated lactic acid bacteria belonging to the strain *Lactococcus lactis* subsp. *lactis* 1526 (DSM 12415).

* * * * *